(12) United States Patent
Iwata et al.

(10) Patent No.: US 6,458,824 B1
(45) Date of Patent: Oct. 1, 2002

(54) SOLID PREPARATION

(75) Inventors: Motokazu Iwata, Takatsuki; Teruaki Kuriyama, Higashiosaka; Megumi Fujita, Otsu; Keiichi Fujiwara, Kyoto; Shiro Kato, Sakai; Hiroshi Harada, Suita; Akihito Fujii, Ikoma; Osamu Odai, Hirakata; Hitoshi Kawashima, Osaka, all of (JP)

(73) Assignee: Dainippon Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/661,577

(22) Filed: Sep. 14, 2000

(30) Foreign Application Priority Data

Nov. 30, 1999 (JP) .......................................... 11-339547

(51) Int. Cl.$^7$ ...................... A61K 31/40; C07D 209/14; A61P 43/00
(52) U.S. Cl. ........................................ 514/415; 548/506
(58) Field of Search ............................ 548/506; 514/415

(56) References Cited

U.S. PATENT DOCUMENTS 5,817,689 A * 10/1998 Kato et al. .................. 514/415

* cited by examiner

*Primary Examiner*—Ceila Chang
*Assistant Examiner*—Andrea D. Small
(74) *Attorney, Agent, or Firm*—Birch, Stewart, Kolasch & Birch, LLP

(57) ABSTRACT

The present invention provides a solid preparation comprising a crystal of [3-[(2R)-[[(2R)-(3-chlorophenyl)-2-hydroxyethyl]amino]propyl]-1H-indol-7-yloxy]acetic acid (Compound A), especially a crystal of Compound A having a particle size of not larger than 100 μm at the cumulative weight distribution value of 50%, and not larger than 200 μm at the cumulative weight distribution value of 95%, preferably a solid preparation having the excellent stability and the content uniformity of Compound A, which is prepared by preparing granules of the crystal of Compound A with fillers, disintegrants and binders, and then followed by mixing said granules with external excipients.

17 Claims, 2 Drawing Sheets

1

SOLID PREPARATION

TECHNICAL FIELD

The present invention relates to a crystal of [3-[(2R)-[[(2R)-(3-chlorophenyl)-2-hydroxyethyl]amino]propyl]-1H-indol-7-yloxy]acetic acid (hereinafter, occasionally referred to as Compound A), and a pharmaceutical preparation containing as a drug substance the crystal of Compound A, especially the present invention relates to a solid preparation wherein the size (volume) of the preparation, the content uniformity of the drug substance, and the stability of the drug substance, are secured, and further the dissolution of the drug substance from the preparation is rapid.

BACKGROUND ART

Compound A exhibits a potent $\beta_3$-adrenergic receptor-stimulating activity with excellent adrenoceptor selectivity, and it is useful in the prophylaxis or treatment of diabetes mellitus and obesity (WO 96/16938).

Compound A exhibits extremely potent pharmaceutical activities, and when it is formulated into a pharmaceutical composition, such composition should be a low-content preparation wherein the content of the active compound per dosage unit is low. However, in compliance with the decrease of the content of Compound A in a preparation, there has been discovered a phenomenon that the chemical stability of Compound A per se is extremely lowered. In addition, when the amount of excipients other than Compound A is increased so that the size being suitable to be used as a pharmaceutical preparation is secured, the content of Compound A per each dosage unit becomes uneven and it is difficult to give a preparation having uniform content of Compound A. Under the circumstances, it has been desired to develop a preparation of Compound A without the above-mentioned defects from which Compound A can rapidly dissolve.

An object of the present invention is to provide a preparation of Compound A wherein the size (cubic capacity) of the preparation, the content uniformity of Compound A, and the stability of Compound A are secured, as well as from which Compound A can rapidly dissolve out.

DISCLOSURE OF INVENTION

The present invention includes the inventions of the following various embodiments.

(1) A crystal of [3-[(2R)-[[(2R)-(3-chlorophenyl)-2-hydroxyethyl]-amino]propyl]-1H-indol-7-yloxy]acetic acid (hereinafter, occasionally referred to as "crystal of Compound A");

(2) A crystal of [3-[(2R)-[[(2R)-(3-chlorophenyl)-2-hydroxyethyl]-amino]propyl]-1H-indol-7-yloxy]acetic acid, which have characteristic diffraction peaks at the diffraction angles (2θ) of about 5.9°, about 17.9°, about 20.5° and about 24.0° in the powder X-ray diffraction pattern (hereinafter, occasionally referred to as "Compound A type-I crystal");

(3) A crystal of Compound A having a particle size of not larger than 100 μm at the cumulative weight distribution value of 50%, and a particle size of not larger than 200 μm at the cumulative weight distribution value of 95% (hereinafter, occasionally referred to as "drug substance");

(4) A granule consisting of the crystal of the above (3) (drug substance);

(5) A granule consisting of (a) a drug substance, (b) a filler, (c) a disintegrant, and (d) a binder;

2

(6) A solid preparation containing the granule of the above (4);

(7) A tablet which is formulated by compressing the granule of the above (4);

(8) A tablet which is formulated by compressing the granule of the above (4) and external excipients;

(9) A $\beta_3$-adrenergic receptor agonist, which comprises the crystal of the above (3) (drug substance);

(10) An agent for treatment of diabetes mellitus, which contains the crystal of the above (3) (drug substance); and

(11) An agent for treatment of obesity, which contains the crystal of the above (3) (drug substance)

Throughout the present description and claims, the "crystal of Compound A" means a pure crystal of 3-[(2R)-[[(2R)-(3-chlorophenyl)-2-hydroxyethyl]amino]propyl]-1H-indol-7-yloxy acetic acid, and as described below, the crystal of Compound A can be grouped into type-1 crystal ("Compound A type-I crystal") and type-II crystal ("Compound A type-II crystal"), based on the diffraction peaks of the powder X-ray diffraction pattern thereof. The type-I crystal, the type-II crystal, or a mixture of these crystals are obtained according to the process for production thereof. The "crystal of compound A" includes all of these crystals.

The "drug substance" means the above crystal of Compound A, having a particle size of not larger than 100 μm at the cumulative weight distribution value of 50%, and a particle size of not larger than 200 μm at the cumulative weight distribution value of 95%. Preferable particle size of the drug substance is not larger than 50 μm at the cumulative weight distribution value of 50%, and not larger than 150 μm at the cumulative weight distribution value of 95%. More preferable particle size is not larger than 30 μm at the cumulative weight distribution value of 50% and not larger than 100 μm at the cumulative weight distribution value of 95%. The "drug substance" of the present invention includes all of these.

The "cumulative weight distribution value" means a value which is obtained by classifying the powders based on the particle size thereof, and by adding up the weights of each particle size from the end of the distribution, and is expressed by percentages to the total weight of the powders. As a method for expressing the mean particle size of the powders (aggregate of particles) having a distribution in the size of particles, the "particle size at the cumulative weight distribution value of 50%" is commonly used. In addition, throughout the present description and claims, the "particle size of the cumulative weight distribution value of 95%" is used as an index for regulating the content of coarse particles which affect the dissolution pattern of the compound from the preparation (see Alfonso R. Gennard (Ed.): Particle Size Measurement and Classification, Remington's Pharmaceutical Sciences 17th edition, Part 8 Chapter 89, pp 1588–1589, 1985; Swithenbank, J., Beer, J. M., Taylot, D. S., Abbot, D. and McCreath, G. C.: A laser diagnostics technique for the measurement of droplet and particle size distribution. AIAA Paper no. 76–79 (1976); and H.ayashi, S.: A laser small angle scattering instrument for the determination of size and concentration distribution in sprays, (Hirleman, E. D. and others Eds.), Liquid particle Size Measurement Techniques: 2nd Volume, Philadelphia, ASTM, 1990).

BEST MODE FOR CARRYING OUT THE INVENTION

Figure 1:
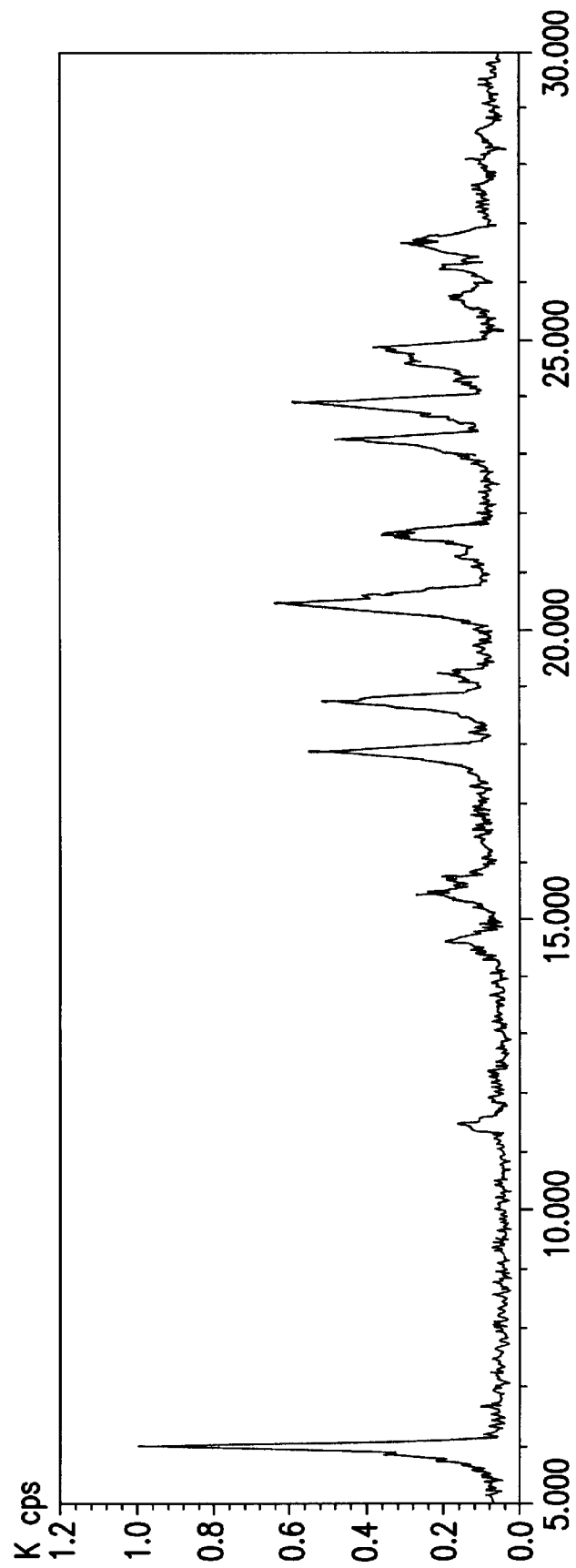
FIG. 1 is the powder X-ray diffraction pattern of Compound A type-I crystal obtained in Preparation 1.

The crystal of Compound A of the present invention may be prepared by the process as illustrated in the following Scheme 1.

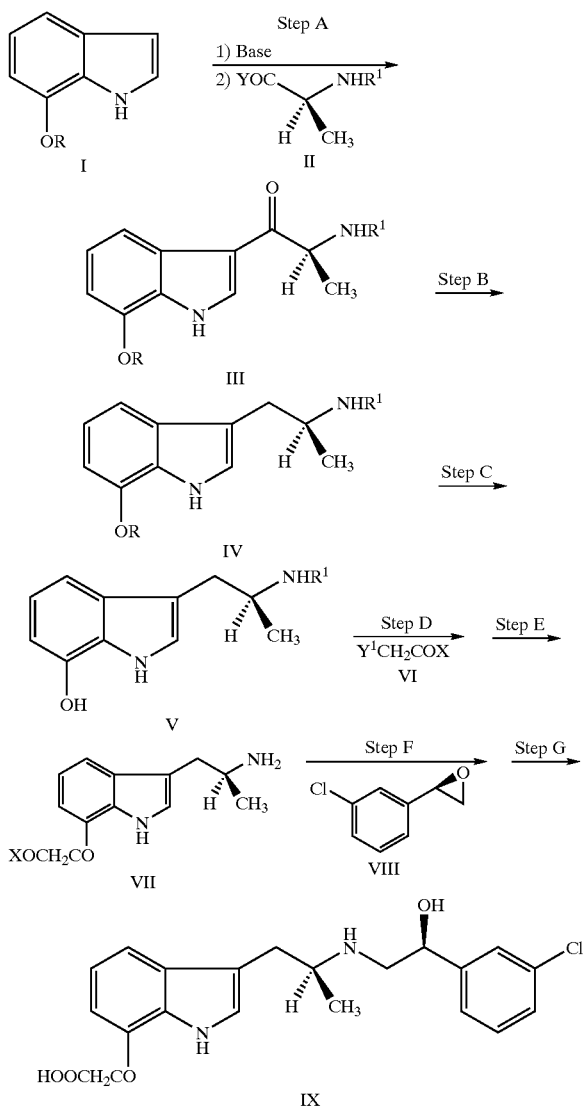

That is, the compound of the formula I (wherein R is a protecting group for phenolic hydroxy group, or —CH$_2$COX, X is a lower alkoxy group, a benzyloxy group, a lower alkyl group, an amino group, a mono- or di-lower alkylamino group, or a cyclic amino group) is reacted with the compound of the formula II (wherein R$^1$ is a protecting group for amino group, and Y is a halogen atom) in the presence of a base to give the compound of the formula III (wherein R and R$^1$ are as defined above). The compound III thus obtained is further reacted with a reducing agent to give the compound of the formula IV (wherein R$^{11}$ is a hydrogen atom or a protecting group for amino group, and R is as defined above). Then, (i) when R of the formula IV is a protecting group for phenolic hydroxy group (and if R$^{11}$ of the formula IV is a hydrogen atom, then the amino group of the compound IV is protected again), the protecting group for phenolic hydroxy group is selectively removed, and the resulting compound of the formula V (wherein R$^1$ is as defined above) is reacted with the compound of the formula VI (wherein Y$^1$ is an alcoholic reactive residue, and X is as defined above), and further the protecting group for amino group is selectively removed to give the compound VII; or (ii) when R of the formula IV is —CH$_2$COX, and R$^{11}$ is a protecting group for amino group, the protecting group for amino group is selectively removed to give the compound VII (wherein X is as defined above), and the resulting compound VII is reacted with the compound of the formula VIII and subsequently the resultant is subjected to hydrogenolysis or hydrolysis under acidic or alkaline conditions to effectively give the crystal of Compound A.

The terms in the process for producing the crystal of Compound A of the present invention are explained below.

The "lower alkyl group" and the "lower alkyl" include a straight chain or branched chain alkyl group having 1 to 6 carbon atoms, for, example, methyl, ethyl, propyl, isopropyl, butyl, and isobutyl, preferably methyl and ethyl, and more preferably methyl.

The "lower alkoxy group" includes a straight chain or branched chain alkoxy group having 1 to 6 carbon atoms, for example, methoxy, ethoxy, propoxy and isopropoxy, preferably methoxy, ethoxy, and propoxy, and more preferably methoxy and ethoxy.

The "mono- or di-lower alkylamino group" includes, for example, methylamino, dimethylamino, ethylamino, methylethylamino, diethylamino, propylamino, isopropylamino, and dipropylamino, preferably methylamino, dimethylamino, ethylamino, diethylamino, and dipropylamino, and more preferably dimethylamino and diethylamino.

The "cyclic amino group" includes a 5- to 7-membered cyclic amino group, for example, pyrrolidinyl, morpholinyl, piperidinyl, and homopiperidinyl, preferably pyrrolidinyl, morpholinyl, and piperidinyl, and more preferably pyrrolidinyl and piperidinyl.

The "protecting group for phenolic hydroxy group and protecting group for amino group" may be conventional protecting groups being used in the organic synthesis field (e.g., T. W. Greene, P. G. M. Muts, Protective Groups in Organic Synthesis, John Wiley & Sons, Inc, Second Edition, 1991, p. 143–170 and p. 309–385), and includes substituents being easily removed by reduction or hydrolysis. A combination of a protecting group for phenolic hydroxy group and a protecting group for amino group should be selected so that one of them can selectively be removed.

The "protecting group for phenolic hydroxy group" includes, for example, methyl, methoxymethyl, methoxyethoxymethyl, tetrahydropyranyl, phenacyl, allyl, isopropyl, tert-butyl, benzyl, diphenylmethyl, triphenylmethyl, acetyl, pivaloyl, benzoyl, methoxycarbonyl, 2,2,2-trichloroethoxycarbonyl, and benzyloxycarbonyl, preferably methyl, tert-butyl, benzyl, diphenylmethyl, triphenylmethyl, and allyl, and more preferably methyl, benzyl, diphenylmethyl, and triphenylmethyl.

The "protecting group for amino group" includes, for example, methoxycarbonyl, ethoxycarbonyl, 2,2,2-trichloroethoxycarbonyl, tert-butoxycarbonyl, benzyloxycarbonyl, vinyloxycarbonyl, 9-fluorenylmethoxycarbonyl, formyl, acetyl, trifluoroacetyl, benzoyl, phthalimido, p-toluenesulfonyl, benzenesulfonyl, methanesulfonyl, and benzyl, preferably tert-butoxycarbonyl, benzyloxycarbonyl, 9-fluorenylmethoxycarbonyl, acetyl, and trifluoroacetyl, and more preferably tert-butoxycarbonyl, benzyloxycarbonyl, and 9-fluorenylmethoxycarbonyl.

The "alcoholic reactive residue" includes, for example, a halogen atom, a lower alkylsulfonyloxy group (e.g., methanesulfonyl, ethanesulfonyl), and an arylsulfonyloxy group (e.g., benzenesulfonyloxy, p-toluenesulfonyloxy).

The "halogen atom" is fluorine atom, chlorine atom, bromine atom, or iodine atom, and preferably chlorine atom.

The process for producing the crystal of Compound A is explained in more detail below.

Step A

Preparation of the Compound of the Formula III:

The compound of the formula III can be prepared by reacting the compound of the formula I with the compound of the formula II in the presence of a base in a suitable solvent.

The base includes, for example, sodium hydride, a metal alkoxide, a Grignard reagent, an alkyl lithium, sodium amide, a lithium dialkylamide, etc. In general, when an indole derivative is reacted with a nucleophilic reagent in the presence of a base, there is obtained a mixture of a 1-substituted compound and a 3-substituted compound. Since a Grignard reagent is widely used in order to preferentially obtain the 3-substituted compound, a Grignard reagent is also preferable in the present step.

The Grignard reagent includes methylmagnesium chloride, methylmagnesium bromide, ethylmagnesium bromide, tert-butylmagnesium chloride, phenylmagnesium chloride, etc., and preferably methylmagnesium bromide and tert-butylmagnesium chloride. The Grignard reagent is usually used in an amount of about 1 to about 8 moles, preferably in an amount of about 2 to about 4 moles, to 1 mole of the compound of the formula I.

The reaction is usually carried out at a temperature of from about −50° C. to about 30° C., preferably at a temperature of from −20° C. to about 0° C. The reaction is preferably carried out under atmosphere of an inert gas such as nitrogen or argon. Besides, an inorganic reagent such as zinc chloride, aluminum chloride, copper bromide, etc. may be added into the reaction system. The solvent may be aromatic hydrocarbons (e.g., benzene, toluene, etc.), ethers (e.g., diethyl ether, tetrahydrofuran, etc.), chloroform, and methylene chloride, and these solvents should be used in an anhydrous form.

The compound of the formula II may be prepared by reacting an amino group-protected α-amino acid with an inorganic halide compound (e.g., phosphorus pentachloride, phosphorus trichloride, phosphorus tribromide, etc.) or an organic halide compound (e.g., phosphoryl chloride, thionyl chloride, oxalyl chloride, phosgene, etc.) in a suitable solvent. The halide compound is used in an amount of about 1 to about 5 moles, preferably in an amount of about 1 to about 2.5 moles, to 1 mole of the starting compound. N,N-Dimethylformamide or hexamethylphosphorous triamide may be added to the reaction system. The reaction is usually carried out at a temperature of from about 0° C. to about 200° C., preferably at a temperature of from about 25° C. to about 130° C. The solvent may be aromatic hydrocarbons (e.g., benzene, toluene, etc.) or halogenated hydrocarbons (e.g., chloroform, methylene chloride, etc.).

Step B

Preparation of the Compound of the Formula IV:

The compound of the formula IV may be prepared by subjecting the compound of the formula III to reduction with an appropriate reducing agent in a suitable solvent. The reducing agent may be, for example, lithium aluminum hydride, sodium bis(2-methoxyethoxy)-aluminum hydride, sodium borohydride, lithium borohydride, calcium borohydride, diborane, aluminum diisobutyl hydride, etc., and preferably an alkali metal borohydride. The reduction of the compound III wherein R is —$CH_2COX$ should be carried out by using a reducing agent that does not reduce the carbonyl group of R. The reducing agent is used in an amount of about 2 to about 6 moles, preferably in an amount of about 3 to about 4 moles, to 1 mole of the compound of the formula III. The reaction temperature may vary depending on the kinds of the reducing agent to be used, but it is usually in the range of about −80° C. to about 150° C., preferably in the range of about 25° C. to about 150° C. The solvent is selected according to the kinds of the reducing agent to be used, and may be ethers (e.g., diethyl ether, tetrahydrofuran, etc.), toluene, chloroform, methylene chloride, methanol, ethanol, isopropanol, acetonitrile, water, etc.

In Step B, when the compound of the formula IV wherein R is a protecting group for phenolic hydroxy group and $R^{11}$ is a hydrogen atom is obtained, said compound is used in the subsequent Step C after the amino group thereof is protected again.

The introduction of a protecting group for amino group is carried out by a conventional method in the peptide synthesis field (i.e., Nobuo IZUMIYA et al., Fundamentals and Experiments of Peptide Synthesis, Maruzene, 1985, p. 16–40). For example, the compound of the formula IV wherein $R^{11}$ is a hydrogen atom is reacted with di-tert-butyl bicarbonate in an appropriate solvent at room temperature to give the compound of the formula IV wherein $R^{11}$ is a tert-butoxycarbonyl group.

In addition, in Step B, when the compound of the formula IV wherein R is —$CH_2COX$ and $R^{11}$ is a protecting group for amino group is obtained, said compound can directly be used in Step E.

Further, in Step B, when the compound of the formula IV wherein R is —$CH_2COX$ and $R^{11}$ is a hydrogen atom is obtained, said compound is identical to the compound of the formula VII, and can directly be used in Step F.

Step C

Preparation of the Compound of the Formula V:

The removal of a protecting group for phenolic hydroxy group of the compound IV wherein $R^{11}$ is a protecting group for amino group and R is a protecting group for phenolic hydroxy group may be carried out by reduction or hydrolysis which should be selected according to the kinds of the protecting group to be removed.

The reductive removal is carried out by hydrogenolysis or by using a metal powder such as zinc powder.

The hydrogenolysis is carried out in the presence of a catalyst such as palladium on carbon, palladium hydroxide, platinum oxide, etc., under hydrogen atmosphere. The reaction is usually carried out at a temperature of from about 20° C. to about 80° C., under atmospheric pressure or under pressure. Catalytic hydrogen transfer reduction using as a hydrogen source ammonium formate, formic acid, cyclohexene, hydrazine, etc. may be employed. The solvent may be alcohols (e.g., methanol, ethanol, etc.), ethyl acetate, acetic acid, water, etc., and these solvents may be used alone or in a mixture of two or more of these solvents.

The hydrolysis is carried out in an appropriate solvent under acid conditions or alkaline conditions. The reaction temperature may vary according to the kinds of the protecting group to be removed, but it is usually in the range of about 0° C. to about 150° C., preferably in the range of about 20° C. to about 100° C. The solvent may be alcohols (e.g., methanol, ethanol, etc.), acetonitrile, water, N,N-dimethylformamide, etc., and these solvents may be used alone or in a mixture of two or more of these solvents. The base may be an alkali metal hydroxide (e.g., sodium hydroxide, potassium hydroxide, etc.) and an organic base (e.g., piperidine, piperazine, etc.), and the acid may be hydrochloric acid, hydrobromic acid,. trifluoroacetic acid, sulfuric acid, formic acid, acetic acid, methanesulfonic acid, etc.

Step D and Step E

Preparation of the Compound of the Formula VII:

The compound of the formula VII is prepared from the compound of the formula V via Steps D and E.

(Step D):

The compound of the formula V and the compound of the formula VI are subjected to addition reaction in an appropriate solvent. The reaction temperature may vary according to the kinds of the starting compounds to be used, and it is usually in the range of about 50° C. to about 200° C. The solvent may be aromatic hydrocarbons (e.g., benzene, toluene, etc.), ketones (e.g., acetone, methyl ethyl ketone, etc.), ethers (e.g., tetrahydrofuran, dioxane, etc.), alcohols (e.g., ethanol, isopropanol, etc.), acetontirile, N,N-dimethylformamide, 1,3-dimethyl-2-imidazolidinone, etc., and these solvents may be used alone or in a mixture of two or more of these solvents.

The reaction may preferably be carried out in the presence of a base. The base may be, for example, an inorganic base such as an alkali metal carbonate (e.g., sodium carbonate, potassium carbonate, etc.), an alkali metal hydrogen carbonate (e.g., sodium hydrogen carbonate, potassium hydrogen carbonate, etc.), an alkali metal hydroxide (e.g., sodium hydroxide, potassium hydroxide, etc.), or an organic base such as triethylamine, tributylamine, N-methylmorpholine, etc. When the compound of the formula VI wherein $Y^1$ is a chlorine atom or a bromine atom is used, the reaction can smoothly proceed by addition of an alkali metal iodide (e.g., sodium iodide, potassium iodide, etc.) or a halogenated tetraalkyl ammonium (e.g., ammonium tetra-n-butyl chloride, etc.).

With utilizing the present reaction, the compound I wherein R is —CH$_2$COX can be prepared from hydroxyindole and the compound of the formula VI in a similar manner.

(Step E):

The compound of the formula VII may be prepared by selectively removing the protecting group for amino group of the compound prepared in Step D.

The protecting group for the amino group is removed by reduction or hydrolysis, which should be selected according to the kinds of the protecting group to be removed.

The reductive removal is carried out by hydrogenolysis or by using a metal powder such as zinc powder.

The hydrogenolysis is carried out in the presence of a catalyst such as palladium on carbon, palladium hydroxide, platinum oxide, etc. under hydrogen atmosphere. The reaction temperature is usually in the range of about 20° C. to about 80° C., under atmospheric pressure or under pressure. Besides, catalytic hydrogen transfer reduction using as a hydrogen source ammonium formate, formic acid, cyclohexene, hydrazine, etc. may also be employed. The solvent may be alcohols (e.g., methanol, ethanol, etc.), ethyl acetate, acetic acid, water, etc., and these solvents may be used alone or in a mixture of two or more of these solvents.

The hydrolysis is carried out under acidic conditions or alkaline conditions in an appropriate solvent. The reaction temperature may vary according to the kinds of the protecting group to be removed, and it is usually in the range of about 0° C. to about 150° C., preferably in the range of about 20° C. to about 100° C. The solvent may be alcohols (e.g., methanol, ethanol, etc.), acetonitrile, water, N,N-dimethylformamide, etc., and these solvents may be used alone or in a mixture of two or more of these solvents. The base may be an alkali metal hydroxide (e.g., sodium hydroxide, potassium hydroxide, etc.), or an organic base such as piperidine, piperazine, etc. The acid may be hydrochloric acid, hydrobromic acid, trifluoroacetic acid, sulfuric acid, formic acid, acetic acid, oxalic acid, methanesulfonic acid, etc.

Step F and Step G

Preparation of the Compound of the Formula IX:

The compound of the formula IX may be prepared from the compound of the formula VII via Steps F and G.

(Step F):

The compound of the formula VII and the compound of the formula VIII are reacted in an appropriate solvent or without a solvent.

The reaction temperature may vary according to the kinds of the starting compounds, and it is usually in the range of about 20° C. to about 150° C., preferably in the range of about 25° C. to about 100° C. The solvent may be aromatic hydrocarbons (e.g., benzene, toluene, etc.), ketones (e.g., acetone, methyl ethyl ketone, etc.), ethers (e.g., tetrahydrofuran, dioxane, etc.), alcohols (e.g., ethanol, isopropanol, etc.), acetonitrile, dimethylsulfoxide, N,N-dimethylformamide, and 1,3-dimethyl-2-imidazolidinone, and these solvents may be used alone or in a mixture of two or more of these solvents. In the reaction system, trimethylsilylacetamide or bistrimethylsilylacetamide may be added.

In the present reaction, instead of the compound of the formula VII, an acid addition salt thereof may be used, and the acid addition salt of the compound VII may be a salt with an inorganic acid such as hydrochloride, hydrobromide, etc., or a salt with an organic acid such as oxalate, maleate, fumarate, etc. When an acid addition salt is used in the present reaction, the reaction is carried out in the presence of a base. The base includes, for example, an inorganic base such as an alkali metal hydrogen carbonate (e.g., sodium hydrogen carbonate, potassium hydrogen carbonate, etc.) and an alkali metal carbonate (e.g., sodium carbonate, potassium carbonate, etc.), or an organic base such as triethylamine, tributylamine, diisopropylethylamine, N-methylmorpholine, etc.

(Step G):

The compound of the formula IX may be prepared by subsequently subjecting the compound obtained in Step F (except for the compound wherein X is a lower alkyl group) to hydrogenolysis in an appropriate solvent, or to hydrolysis under acidic or alkaline conditions.

The hydrogenolysis is carried out in the presence of a catalyst such as palladium on carbon, palladium hydroxide, platinum oxide, etc., under hydrogen atmosphere. The reaction is carried out at a temperature of from about 20° C. to about 80° C. under atmospheric pressure or under pressure. Catalytic hydrogen transfer reduction using as a hydrogen source ammonium formate, formic acid, cyclohexene, hydrazine, etc. may also be employed. The solvent may be alcohols (e.g., methanol, ethanol, etc.), ethyl acetate, acetic acid, water, etc., and these solvents may be used alone or in a mixture of two or more of these solvents.

The hydrolysis is carried out in a solvent under acidic or alkaline conditions. The reaction temperature may vary according to the kinds of the starting compounds, and it is usually in the range of about 0° C. to about 150° C., preferably in the range of about 20° C. to about 80° C. The solvent may be alcohols (e.g., methanol, ethanol, isopropanol, etc.), dioxane, water, or a mixture of these solvents. The acid includes, for example, an inorganic acid such as hydrochloric acid, hydrobromic acid, hydroiodic acid, sulfuric acid, etc., and an organic acid such as fornic acid, acetic acid, trifluoroacetic acid, p-toluenesulfonic acid, methane-sulfonic acid, etc. The base includes, for example, an alkali metal hydroxide (e.g., sodium hydroxide, potassium hydroxide, etc.), and an alkali metal carbonate (e.g., sodium carbonate, potassium carbonate, etc.).

The crystal of Compound A thus obtained is Compound A type-I crystal showing characteristic diffraction peaks at the diffraction angles (2θ) of about 5.9°, about 17.9°, about 20.5°, and about 24.0° in the powder X ray diffraction pattern.

The Compound A type-I crystal is recrytallized from a solvent such as methanol to give the crystal showing characteristic diffraction peaks at the diffraction angles (2θ) of about 5.9°, about 17.5°, about 20.8°, and about 23.3° (Compound A type-II crystal), but Compound A type-I crystal is more easily produced industrially than Compound A type-II crystal.

In the preparation of the present invention, the crystal of Compound A having a particle size of not larger than 100 μm at the cumulative weight distribution value of 50%, and a particle size of not larger than 200 μm at the cumulative weight distribution value of 95%, i.e., drug substance, is used. Preferably, ones having a particle size of not larger than 50 μm at the cumulative weight distribution value of 50%, and a particle size of not larger than 150 μm at the cumulative weight distribution value of 95%, more preferably ones having a particle size of not larger than 30 μm at the cumulative weight distribution value of 50%, and a particle size of not larger than 100 μm at the cumulative weight distribution value of 95% are used. By using a drug substance satisfying the above requirements, a preparation from which the drug substance rapidly dissolve can be obtained. Besides, since a drug substance may optionally be obtained as an agglomerate, it is preferable that the drug substance has a content of said agglomerate of less than 50%, and almost single particle size distribution.

The particle sizes of the drug substance (at the cumulative weight distribution values of 50% and 95%) are measured by a conventional method for measurement of particle size of medicaments, for example, by a. standard sieving method, sedimentation method, light scattering method, image analysis, etc., but the method for measuring should not be limited to these methods.

The present drug substance satisfying the above requirements may be obtained by selecting the crystallization conditions in the synthesis process of Compound A and/or by selecting the pulverizing method after the synthesis of Compound A. For instance, after the synthesis of Compound A, a drug substance can be obtained by pulverizing Compound A by a hammer mill, a fluid energy mill, a planetary ball mill, a vibrating ball mill, a conical ball mill, a roller mill, or a pin mill, under conditions which are selected according to the mill to be used. A drug substance can be obtained by controlling the particle size and the agglutination rate of Compound A during the synthesis process thereof, or by dissolving the precipitated crystals during the synthesis process in an appropriate solvent such as water, an organic solvent, etc., and subjecting the resulting solution to spray-drying or drying in supercritical fluid of carbon dioxide gas, under the selected conditions.

For preparing the desired pharmaceutical preparation using the drug substance thus obtained, granules containing said drug substance are prepared.

The granules can contain, in addition to (a) a drug substance, (b) a filler, (c) a disintegrant, and (d) a binder, but further can contain a glidant, a lubricant, etc.

Since the excipients other than the drug substance in the granules directly contact the drug substance, it is preferable to use such excipients compatible with the drug substance and to incorporate them in a suitable ratio to the drug substance, by which the stability of the drug substance is secured. The excipients other than the drug substance in the granules include, for example, a filler, a disintegrant, and a binder, but if necessary, a glidant, a lubricant, etc. may be used as an excipient.

The excipients other than the drug substance in the granules are usually contained in an amount of 500 parts by weight or less, preferably in an amount of 300 parts by weight or less, more preferably in an amount of 100 parts by weight or less, to 1 part by weight of the drug substance.

The filler includes, for example, lactose, corn starch, sucrose, trehalose, D-mannitol, erythritol, maltitole, and ethyl cellulose. The disintegrant includes, for example, low-substituted hydroxypropylcellulose, carmellose calcium, and crosscarmellose sodium. The binder includes, for example, hydroxypropylcellulose, hydroxypropylmethylcellulose, pullulan, polyvinyl pyrrolidone, gelatin, and carmellose sodium.

The glidant and the lubricant include, for example, magnesium stearate, hydrogenated castor oil, light anhydrous silicic acid, and talc. When magnesium stearate is used, it is used in an amount of 1% to 5% part by weight, preferably in an amount of 1% to 4% part by weight, more preferably in an amount of 1.5% to 3% part by weight, based on the total weight of the preparation.

The preparation of the granules is preferably carried out by preparing previously a preparatory mixing powder of the drug substance and a part or whole of fillers by mixing them, followed by sieving or pulverizing, and then adding thereto the remaining excipients, and if necessary, followed by granulating or regulating the size of the mixture, by which the content uniformity of the drug substance is secured.

The mixing and sieving is carried out by hand using a. sieve of 24 to 60 mesh, or by using a sieving apparatus having a suitable mixing capacity such as an oscillator. The mixing and pulverizing is carried out using a pulverizer such as a hammer mill.

The granulation is carried out, for example, by wet-granulation using fluid bed granulator, agitation granulator, or high-shear granulator.

The particle size of the granules thus prepared is usually not larger than 350 μm at the cumulative weight distribution value of 50%, and not larger than 1400 μm at the cumulative weight distribution value of 95%. Preferably, the particle size of the granules is not larger than 300 μm at the cumulative weight distribution value 50%, and not larger than 1000 μm at the cumulative weight distribution value of 95%. More preferably, the particle size of the granules is not larger than 250 μm at the cumulative weight distribution value of 50%, and not larger than 800 μm at the cumulative weight distribution value of 95%. By using granules having such a preferable particle size, the content uniformity of the drug substance is more secured.

The particle sizes of the drug substance (at the cumulative weight distribution values of 50% and 95%) are measured by a conventional method for measurement of particle size of medicaments, for example, by a standard sieving method, sedimentation method, light scattering method, image analysis, etc., but the method for measuring should not be limited to these methods.

The solid preparation of the present invention contains the granules thus obtained. The solid preparation may be, for example, tablets, capsules, granules, powders, suppositories, or external preparations such as adhesive tape.

The solid preparation may contain only the granules, but in the low-content preparation containing 2 mg or less of the drug substance per dosage unit, it is preferable to increase the volume (weight) of the preparation by adding external excipients into the granules in order to secure the sufficient stability of the drug substance as well as to secure a suitable size (usually 4 to 10 mm of diameter, 25 to 300 mg).

The external excipient may be, for example, in addition to the excipients such as fillers, disintegrants, binders that can be used in the production of the granules, crystalline cellulose as a filler.

In order to secure the content uniformity of the drug substance, the external excipients are contained in an amount of 0.01 to 100 parts by weight, preferably in an amount of 0.10 to 50 parts by weight, more preferably in an amount of 0.15 to 10 parts by weight, to 1 part by weight of the granules.

In formulating the preparation, the external excipients may be used for mixing with the drug substance containing granules merely as a mixture of the external excipients, or after granulating the external excipients or regulating in size thereof to the same particle size as those of the granules. For granulation or regulation in size of the external excipients, hydroxypropylcellulose, hydroxypropylmethylcellulose, pullulan, polyvinylpyrrolidone, gelatin, carmellose sodium may be used as a binder. When mixing the granules and the external excipients, a glidant and/or lubricant may be used.

The granules and the external excipients may be compressed together without mixing to give dry coated tablets or multilayer tablets. In this case, the external excipients may be, for example, crystalline cellulose and/or low substituted hydroxypropylcellulose and magnesium stearate and/or hydrogenated castor oil. Moreover, light anhydrous silicic acid and/or talc may be used. If necessary, hydroxypropylcellulose, hydroxypropylmethylcellulose, or pullulan may be used as a binder.

When tableting the granules or a mixture of the granules and the external excipients, it is preferable to add magnesium stearate or hydrogenated castor oil in an amount of 1% to 5% by weight to the granules or a mixture of the granules and the external excipients, in order to prevent sticking which may easily occur in the compression tableting procedure, and then the mixture thus obtained is subjected to compression tableting with a suitable tableting machine to give the desired tablets.

In addition, in order to mask bad tastes, to increase the strength of tablets, to improve a feeling when taken, and to increase the easiness when used, the tablets thus obtained may be coated with a suitable polymeric ingredient to give film coated tablets. The polymeric ingredient may be, for example, hydroxypropylmethylcellulose, hydroxypropylcellulose, hydroxyethylcellulose, methylhydroxyethylcellulose, methyl cellulose, ethyl cellulose, carmellose sodium, polyvinylpyrrolidone, polyvinyl alcohol, polyethylene glycol, dimethylaminoethyl metacrylate-methyl acrylate copolymer, and ethyl acrylate-methyl metacrylate copolymer. If necessary, as a plasticizer for the polymeric ingredient, for example, propyleneglycol, glycerol, polyethyleneglycol, glyceryl triacetate (triacetin), triethyl citrate, acetyltriethyl citrate, diethyl phthalate, diethyl sebacate, acetylated monoglyceride, castor oil, or liquid paraffin may be added into a coating agent. Further, in order to protect from light or to improve the discriminability, a suitable coloring agent may be added into a coating agent. The coloring agent may be, for example, a water-soluble synthetic pigment such as Yellow No. 4, Yellow No. 5, Blue No. 1, Blue No. 2, etc., and their aluminum lakes, talc, titanium oxide, iron oxides, calcium sulfate, calcium carbonate, or riboflavin, carmine, turmeric pigment may be added. Moreover, in order to increase palatability, a sweetening agent or a flavor may be added as well.

In addition, the tablets may be converted into sugar coated tablets for the same purpose as mentioned above. The sugar coating agent may consist of, in addition of the main component of sucrose or sorbitol, calcium carbonate, talc or titanium oxide, and further contains as a binder, for example, gelatin, acacia, polyvinyl alcohol, etc., or a cellulose derivative such as pullulan, hydroxypropylmethylcellulose, etc., and if necessary, a water-soluble synthetic pigment such as Yellow No. 4, Yellow No. 5, Blue No. 1, Blue No. 2, etc., and their aluminum lakes, talc, titanium oxide, iron oxides, calcium sulfate, calcium carbonate, or riboflavin, carmine, turmeric pigment may be added. Moreover, in order to increase palatability, a sweetening agent or a flavor may be added as well.

The granules or a mixture of the granules and the external excipients may directly be formulated into fine granule preparations, granule preparations or powder preparations, or into capsule preparations by filing them in gelatin capsules. In this case, the external excipients may be, for example, lactose, corn starch, sucrose, trehalose, D-mannitol, erythritol, maltitole, and/or ethyl cellulose, and magnesium stearate and/or hydrogenated castor oil. Further, light anhydrous silicic acid and/or talc may be used as well. In the case of granule preparations, after granulating, hydroxypropylcellulose, hydroxypropylmethylcellulose, pullulan, polyvinylpyrrolidone, gelatin, or carmelose sodium may be added as a filler for granule preparations.

If further necessary, in order to make the tablets sustained release ones, the drug substance-containing granules or tablets are coated with a coating gent for controlling the release of a medicament consisting of a polymeric ingredient or fats and oils to give reservoir type sustained release tablets. The coating agent may be, for example, beeswax, carnauba wax, cetyl alcohol, cetylstearyl alcohol, lipid-fats and oils, resins (e.g., shellac), cellulose esters (e.g., ethyl cellulose), and acrylic acid esters. If necessary, as a plasticizer for the polymeric ingredient, propylene glycol, glycerol, polyethylene glycol, glyceryl triacetate (triacetin), triethyl citrate, acetyltriethyl citrate, diethyl phthalate, diethyl sebacate, acetylated monoglyceride, castor oil, or liquid paraffin may be added into a coating agent. Further, in order to protect from light or to improve the discriminability, a suitable coloring agent may be added into a coating agent. The coloring agent may be, for example, a water-soluble synthetic pigment such as Yellow No. 4, Yellow No. 5, Blue No. 1, Blue No. 2, etc., and their aluminum lakes, talc, titanium oxide, iron oxides, calcium sulfate, calcium. carbonate, or riboflavin, carmine, turmeric pigment may be added. Moreover, in order to increase palatability, a sweetening agent or a flavor may be added as well. In addition, the granules controlling the release of the medicament may be compressed to give tablets.

There may be obtained a matrix type sustained release preparation by mixing a component for controlling the release of medicament such as the polymeric ingredients as mentioned above or fats and oils together with fillers in the step of producing granules and tablets. Further, if necessary, the granules thus controlled in the release of medicament can be compressed to give tablets.

The solid preparation of the present invention thus obtained may be packed, if necessary, in blister pack, heat-seal pack, or bottles of suitable materials, but should not be limited to these packages. Further, if necessary, the solid preparation of the present invention may be packed together with a suitable desiccant such as silica gel.

PHARMACEUTICAL EXPERIMENT

The effect on human β-adrenergic receptors of the drug substance of the present invention was studied.

The cell lines highly expressing human $\beta_3$- and $\beta_2$-adrenergic receptors were prepared according to the method disclosed in WO 96/16938. The cell line highly expressing human $\beta_1$-adrenergic receptor was prepared according to the method disclosed in WO 00/44721.

Experiment

Human $\beta_3$-adrenergic receptor-stimulating activity:

Human $\beta_3$-adrenergic receptor-highly expressing cell line CHO/pKREX10-36 was cultured for 2–3 days with MEM-Dulbecco's medium supplemented with 10% fetal bovine serum and 200 μg/ml G-418. The cells were peeled off by incubation with phosphate-buffered saline containing 0.5 mM EDTA at 37° C. for 10 minutes after the medium was removed. The CHO/pKREX10-36 cells were collected by centrifugation, and suspended in Hanks' buffer (ICN Biomedicals) containing 1 mM L-ascorbic acid and 1 mM 3-isobutyl-1-methylxanthine at the concentration of about $5\times10^5$ cells/ml. This suspension (100 μl) and a test compound were mixed in the same buffer (500 μl) and incubated at 37° C. for 30 minutes, followed by boiling for 5 minutes to terminate the reaction. After centrifugation of the reaction mixture, the amount of cAMP in the supernatant was measured by using cAMP EIA System (Amersham).

Similarly, the amount of cAMP was measured in the same manner by using CHO/pKREX21-8 for highly expressing human $\beta_2$-adrenergic receptor, or by using CHO/pKREX23-30 for highly expressing human $\beta_1$-adrenergic receptor instead of the CHO/pKREX10-36 for highly expressing human $\beta_3$-adrenergic receptor.

The amounts of cAMP when adding $10^{-5}$ M of (−)-isoproterenol to the reaction mixture or not adding thereof at all were designated as 100% and 0%, respectively, and the relative maximal response of the drug substance of the present preparation ($10^{-6}$ to $10^{-11}$ M) is expressed as intrinsic activity [I.A.]. $EC_{50}$ value which is a concentration of the test compound to be required to achieve 50% of cAMP accumulation was calculated by least squares regression analysis of a concentration-response curve of each compound.

The results are shown in Table 1.

TABLE 1

| | Human $\beta_3$-, $\beta_2$- and $\beta_1$-adrenergic receptor-stimulating activity | | | | | |
|---|---|---|---|---|---|---|
| Test | $\beta_3$-receptor | | $\beta_2$-receptor | | $\beta_1$-receptor | |
| Comp. | $EC_{50}$ (nM) | I.A. (%) | $EC_{50}$ (nM) | I.A. (%) | $EC_{50}$ (nM) | I.A. (%) |
| A* | 0.27 | 110 | 21 | 45 | 3.5 | 83 |
| IP** | 10 | 100 | 4.2 | 100 | 0.46 | 100 |

Note: *means drug substance; **means (-)-isoproterenol.

In this experiment, a compound having a low $EC_{50}$ value and a high I.A. value is considered to have a potent human β-adrenergic receptor-stimulating activity. Thus, as is clear from Table 1, the drug substance of the present preparation is proven to have a potent stimulating activity of human $\beta_3$-adrenergic receptor, but the stimulating activity of human $\beta_2$- and $\beta_1$-adrenergic receptors thereof is quite weak.

As is shown in the above results, the drug substance of the present invention can be expected as a human $\beta_3$-adrenergic receptor-stimulating agent with excellent adrenoceptor selectivity.

The drug substance of the present invention is useful as a $\beta_3$-adrenergic receptor-stimulating agent in the prophylaxis or treatment of obesity, diabetes mellitus, hyperlipemia, irritable bowel syndrome, acute or chronic diarrhea, pollakisuria, enuresis, urinary calculus, etc. Besides, the drug substance of the present invention is also useful in the improvement of the symptoms such as stomach ache, nausea, vomiting, epigastrium sickness, accompanying with peptic ulcer, acute or chronic gastritis, biliary dyskinesia, cholecystitis, etc.

When the drug substance of the present invention is used as a $\beta_3$-adrenergic receptor-stimulating agent, it may be administered orally, parenterally, or rectally, but preferably by oral route. The dose of the drug substance of the present invention may vary according to the administration route, the conditions, ages of the patients, or kinds of objects (prophylaxis or treatment), etc., but it is usually in the range of 0.0002 mg/kg/day to 0.02 mg/kg/day, preferably in the range of 0.001 mg/kg/day to 0.02 mg/kg/day.

BEST MODE FOR CARRYING OUT THE INVENTION

EXAMPLES

The present invention is illustrated in more detail by the following Preparations, Experiments, and Examples, but should not be construed to be limited thereto.

Preparation 1
Preparation of crystal of Compound A:

The identification of the compounds was carried out by Elementary analysis, Mass spectrum analysis, Infrared (IR) absorption spectrum, Proton nuclear magnetic resonance (1H-NMR) spectrum, and by measurement of optical rotation. The optical purity was determined by high performance liquid chromatography.

The following abbreviations may be used in order to simplify the disclosure.

Fmoc: 9-Fluorenylmethoxycarbonyl group
Ala: Alanine residue
J: Coupling constant
s: Singlet
d: Doublet dd: Double doublet
t: Triplet
q: Quartet
m: Multiplet
br: Broad (1) Preparation of (R)-3-(2-Aminopropyl)-7-Benzyloxyindole Oxalate (Step 1)

To a suspension of Fmoc-D-Ala-OH (23.35 g, 75 mmol), methylene chloride (240 ml) and N,N-dimethylformamide (0.39 ml) was added dropwise oxalyl chloride (7 ml, 80 mmol) at room temperature under stirring, and the mixture was further stirred for one hour. The reaction mixture was concentrated to dryness under reduced pressure to give a solid containing Fmoc-D-Ala-Cl, which was used in the subsequent reaction without further purification.

(Step 2)

To an ice cooled and stirred solution of commercially available 7-benzyloxyindole (11.2 g, 50 mmol) in methylene chloride (100 ml) was added a 3 M diethyl ether solution of methylmagnesium bromide (50 ml, 150 mmol) under argon atmosphere. The mixture was warmed to room temperature and further stirred for one hour. To the reaction mixture was added dropwise a solution of Fmoc-D-Ala-Cl obtained in Step 1 in methylene chloride (200 ml) under ice-cooling. The mixture was warmed to room temperature and further stirred for one hour. To the mixture was added 5% aqueous hydrochloric acid solution (100 ml) under ice-cooling, and the whole was stirred for 15 minutes. The organic layer was separated, washed with water (100 ml), and dried over anhydrous magnesium sulfate. The solvent was evaporated under reduced pressure to give an oil (40.05 g) containing (R)-7-benzyloxy-3-[[2-(9-fluorenylmethoxycarbonyl)amino]propionyl]indole, which was further used in the subsequent Step without further purification.

(Step 3)

To a stirred mixture of the oil obtained in Step 2 in a mixture of acetonitrile (100 ml) and 2-propanol (15.03 ml) was added portionwise sodium borohydride (5.67 g, 150 mmol) at room temperature, and the mixture was refluxed for 5 hours. The reaction mixture was cooled to room temperature, and thereto was added dropwise methanol (100 ml). The reaction mixture was concentrated to dryness under reduced pressure. After addition of ethyl acetate (250 ml) and water (100 ml) to the residue, the mixture was stirred. The organic layer was separated, washed with water (100 ml), and dried over anhydrous magnesium sulfate. The inorganic materials were removed, and to the resultant was added with stirring a solution of oxalic acid (4.50 g, 50 mmol) in ethyl acetate (45 ml) at room temperature. The precipitated crystals were collected by filtration, washed with ethyl acetate, and dried to give the title compound (11.2 g, 61%) as white crystals, m.p. 206–208° C.

$[\alpha]D^{25}$=−46.2° (c=1.0, N,N-dimethylformamide); $^1$H-NMR spectrum (200 MHz, DMSO-$d_6$, δ ppm): 1.14 (3H, d, J=7 Hz), 2.80 (1H, dd, J=14 Hz, J=8 Hz), 3.03 (1H, dd, J=14 Hz, J=5 Hz), 3.42 (1H, m), 5.26 (2H, s), 5.94 (4H, br), 6.75 (1H, d, J=8 Hz), 6.92 (1H, t, J=8 Hz), 7.11–7.22 (2H, m), 7.32–7.48 (3H, m), 7.51–7.62 (2H, m), 11.11 (1H, s).

(2) Preparation of (R)-3-(2-Tert-butoxycarbonylaminopropyl)-7-benzyloxyindole

To a mixture of potassium carbonate (28 g), water (500 ml) and ethyl acetate (250 ml) was added (R)-3-(2-aminopropyl)-7-benzyloxyindole oxalate (50 g, 135 mmol) obtained in the above (1), and the mixture was stirred. Then, to the ice cooled and stirred mixture was added di-tert-butyl bicarbonate (29.5 g, 135 mmol), and the mixture was stirred at room temperature for 3 hours. The organic layer was separated, washed with a saturated aqueous sodium chloride solution (150 ml), and dried over anhydrous magnesium sulfate. The solvent was evaporated under reduced pressure, and to the residue was added n-hexane (150 ml). The precipitated crystals were collected by filtration and dried to give the title compound (47.2 g, 92%) as white crystals, m.p. 94–95° C.

$[\alpha]D^{25}$=−21.0° (c=1.0, methanol); $^1$H-NMR spectrum (300 MHz, $CHCl_3$, δ ppm): 1.11 (3H, d, J=6.6 Hz), 1.43 (9H, s), 2.83 (1H, dd, J=14.5 Hz, J=6.7 Hz), 2.94 (1H, dd, J=14.5 Hz, J=5.1 Hz), 4.00 (1H, m), 4.44 (1H, m), 5.18 (2H, s), 6.71 (1H, d, J=7.5 Hz), 6.97 (1H, d, J=2.2 Hz), 7.02 (1H, t, J=7.9 Hz), 7.20 (1H, s), 7.24–7.51 (5H, m), 8.30 (1H, s).

Optical purity: 98.5% ee [conditions for analysis; Column (CHIRALPAK AD (diameter 4.6 mm×250 mm: manufactured by DAICEL CHEMICAL INDUSTRIES, LTD.)); Mobile phase (n-hexane: isopropanol=70:30); Flow rate (0.8 ml/min); Temperature (25° C.); Wave length for Detection (254 nm); Retention time (8.8 min.)]

(3) Preparation of N,N-diethyl-[3-[[(2R)-tert-butoxycarbonylamino]-propyl]-1H-indol-7-yloxy]acetamide To an ice cooled and stirred solution of (R)-7-benzyloxy-3-(2-tert-butoxycarbonylaminopropyl)indole (10 g, 26.3 mmol) obtained in the above (2) in methanol (100 ml) was added 10% palladium on carbon (0.5 g), and the mixture was hydrogenated under atmospheric pressure of hydrogen at room temperature for 2 hours. After the theoretical amount of hydrogen gas was consumed, the catalyst was removed, and the solvent was evaporated under reduced pressure. The residue was dissolved in acetone (60 ml), and to the solution were added potassium carbonate (4.54 g), N,N-diethylchloroacetamide (4.72 g, 31.6 mmol) and potassium iodide (0.55 g), and the mixture was refluxed for 4 hours. After ice-cooling, the insoluble materials were removed by filtration, and the solvent was evaporated under reduced pressure. To the residue were added chloroform (100 ml) and water (100 ml), and the mixture was stirred. The chloroform layer was separated and dried over anhydrous magnesium sulfate. The solvent was evaporated under reduced pressure, and to the residue was added diisopropyl ether (30 ml). The precipitated crystals were collected by filtration and dried to give the title compound (10.7 g, 100%) as white crystals, m.p. 142° C.

$[\alpha]D^{25}$=−26.3° (c=1.0, methanol); $^1$H-NMR spectrum (300 MHz, $CDCl_3$, δ ppm): 1.10 (3H, d, J=6.6 Hz), 1.17 (3H, t, J=7.1 Hz), 1.22 (3H, t, J=7.1 Hz), 1.43 (9H, s), 2.83 (1H, dd, J=14.1 Hz, J=7.0 Hz), 2.94 (1H, dd, J=14.1 Hz, J=5.1 Hz), 3.34 (2H, q, J=7.1 Hz), 3.44 (2H, q, J=7.1 Hz), 3.99 (1H, br), 4.45 (1H, br), 4.80 (2H, s), 6.67 (1H, d, J=7.7 Hz), 6.99 (1H, t, J=7.9 Hz), 7.10 (1H, s), 7.30 (1H, d, J=7.9 Hz), 9.41 (1H, s).

Optical purity: >99% ee [conditions for analysis; Column (CHIRALPAK AD (diameter 4.6 mm×250 mm: manufactured by DAICEL CHEMICAL INDUSTRIES, LTD.)); Mobile phase (n-hexane:isopropanol=50: 50); Flow rate (0.8 ml/min); Temperature (25° C.); Wave length for Detection (254 nm); Retention time (6.6 min.)]

(4) Preparation of N,N-diethyl-[3-[(2R)-Aminopropy]-1H-indol-7-yloxy]acetamide

To a solution of N,N-diethyl-[3-[[(2R)-tert-butoxycarbonylamino]propy]-1H-indol-7-yloxy]acetamide (12 g, 29.7 mmol) obtained in the above (3) in acetonitrile (120 ml) was added oxalic acid (10.71 g, 119 mmol), and the mixture was refluxed for 2 hours. The mixture was cooled with ice, and the precipitated crystals were collected by filtration and washed with acetonitrile. To the resulting crystals were added 10% aqueous potassium carbonate solution (50 ml) and chloroform (120 ml), and the mixture was stirred. The chloroform layer was separated and dried over anhydrous magnesium sulfate. The solvent was evaporated under reduced pressure, and to the residue was added diisopropyl ether (30 ml). The precipitated crystals were collected by filtration and dried to give the title compound (6.84 g, 75%) as white crystals, m.p. 133° C.

$[\alpha]D^{25}$=−46.3° (c=1.0, methanol); $^1$H-NMR spectrum (300 MHz, $CDCl_3$, δ ppm): 1.16 (3H, d, J=6.6 Hz), 1.17 (3H, t, J=7.1 Hz), 1.22 (3H, t, J=7.1 Hz), 1.40–2.00 (2H, br), 2.64 (1H, dd, J=14.1 Hz, J=8.2 Hz), 2.86(1H, dd, J=14.1 Hz, J=5.0 Hz), 3.18 (1H, m), 3.35 (2H, q, J=7.1 Hz), 3.44 (2H, q, J=7.1 Hz), 4.80 (2H, s), 6.68 (1H, d, J=7.5 Hz), 6.99 (1H, t, J=7.9 Hz), 7.05 (1H, s), 7.28 (1H, d, J=8.0 Hz), 9.42 (1H, s).

Optical purity: >99% ee [conditions for analysis; Column (CHIRALPAK AD (diameter 4.6 mm×250 mm: manufactured by DAICEL CHEMICAL INDUSTRIES, LTD.)); Mobile phase (n-hexane:isopropanol:diethylamine= 85:15:0.8); Flow rate (1.0 ml/min); Temperature (25° C.); Wave length for Detection (254 nm); Retention time (19.9 min.)]

(5) Preparation of N,N-diethyl-[3-[(2R)-[[(2R)-(3-chlorophenyl)-2-hydroxyethyl]amino]propyl]-1H-indol-7-yloxy]acetamide To a solution of N,N-diethyl-[3-[(2R)-aminopropy]-1H-indol-7-yloxy]acetamide (21 g, 69.2 mmol) obtained in the above (4) in acetonitrile (42 ml) was added (R)-3-chlorostylene oxide (11.77 g, 76.1 mmol), and the mixture was refluxed for 5 hours. The mixture was cooled with ice, and thereto was added diisopropyl ether (168 ml). The precipitated crystals were collected by filtration and dried to give the title compound (16.99 g, 54%) as white crystals. On the other hand, the filtrate containing the unreacted starting materials was concentrated to dryness under reduced pressure, and to the residue were added again acetonitrile (21 ml) and (R)-3-chlorostyrene oxide (1.07 g, 6.9 mmol), and the mixture was refluxed for 6 hours. The mixture was cooled with ice, and thereto was added diisopropyl ether (63 ml). The precipitated crystals were collected by filtration and dried to give the title compound (2.86 g, 9%), m.p. 120–121° C.

$[\alpha]D^{25}$=−69.1° (c=1.0, methanol); $^1$H-NMR spectrum (300 MHz, $CDCl_3$, δ ppm): 1.11 (3H, d, J=6.2 Hz), 1.16 (3H, t, J=7.1 Hz), 1.22 (3H, t, J=7.1 Hz), 2.66 (1H, dd, J=12.2 Hz, J=9.2 Hz), 2.81 (2H, d, J=6.6 Hz), 2.87 (1H, dd, J=12.2 Hz, J=3.7 Hz), 3.00 (1H, m), 3.34 (2H, q, J=7.1 Hz), 3.43 (2H, q, J=7.1 Hz), 4.54 (1H, m), 4.78 (2H, s), 6.65 (1H, d, J=7.3 Hz), 6.98 (1H, t, J=7.9 Hz) 6.99 (1H, s), 7.12–7.30 (4H, m), 7.34 (1H, s), 9.60 (1H, s).

(6) Preparation of [3-[(2R)-[[(2R)-(3-chlorophenyl)-2-hydroxyethyl]-amino]propyl]-1H-indol-7-yloxy] acetic acid (Compound A)

N,N-Diethyl-[3-[(2R)-[[(2R)-(3-chlorophenyl)-2-hydroxyethyl]-amino]propyl]-1H-indol-7-yloxy]acetamide (4 g, 8.7 mmol) obtained in the above (5) was added to a solution of potassium hydroxide (1.96 g, 34.9 mmol) in 50% aqueous ethanol solution (32 ml), and the mixture was refluxed for 3 hours and cooled to room temperature. The mixture was dissolved in acetic acid (2.3 g, 38.4 mmol) and stirred at room temperature overnight. The precipitated crystals were collected by filtration, and dried to give the title compound (3.1 g, 88%) as white crystals, m.p. 230–231° C.

$[\alpha]D^{25}$=−24.40 (c=1.0, 1 N aqueous sodium hydroxide solution); $^1$H-NMR spectrum (200 MHz, DMSO-$d_6$, δ ppm): 0.93 (3H, d, J=7 Hz), 2.61 (1H, m), 2.80–3.22 (4H, m), 4.54 (2H, s), 4.90 (1H, m), 6.48 (1H, d, J=8 Hz), 6.76 (1H, t, J=8 Hz), 6.89–7.02 (2H, m), 7.28–7.40 (3H, m), 7.46 (1H, s), 11.01 (1H, s).

Optical purity: >99% ee [conditions for analysis; Column (CHIRAL-AGP (diameter 4.0 mm×100 mm: manufactured by SHINWA KAKO CO., LTD.)); Mobile phase (aqueous (20 mM Na2HPO$_4$+2 mM ammonium tetrabutyl hydrogen sulfite) solution (pH 7.0):isopropanol=98:2); Flow rate (0.7 ml/min); Temperature (30° C.); Wave length for Detection (220 nm); Retention time (27.4 min.)]

The X-ray diffraction pattern of the crystals of Compound A thus obtained was measured with an X-ray powder diffractometer (RINT1000-type; manufactured by RIGAKU CORPORATION) at a tube voltage of 30 kV, and a tube electric current of 20 mA using CuKa wire in terms of diffraction angle (2θ). The diffraction pattern thereof is shown in FIG. 1. The diffraction angles in the X-ray powder diffraction pattern of the crystals of Compound A are about 5.9°, about 17.9°, about 18.8°, about 20.5°, about 23.3°, about 24.0°, and about 24.9°, and there are characteristic peaks at about 5.9°, about 17.9°, about 20.5°, and about 24.0°. The values of the diffraction angle (2θ) have the standard accuracy.

Preparation 2
Preparation of Compound A Type-II Crystals:
To the Compound A Type-I crystals (100 mg) obtained in Preparation 1 was added methanol (35 ml), and the mixture was dissolved with warming in a water bath at 100° C. The precipitated crystals were collected by filtration, and dried to give Compound A Type-II crystals.

Figure 2:
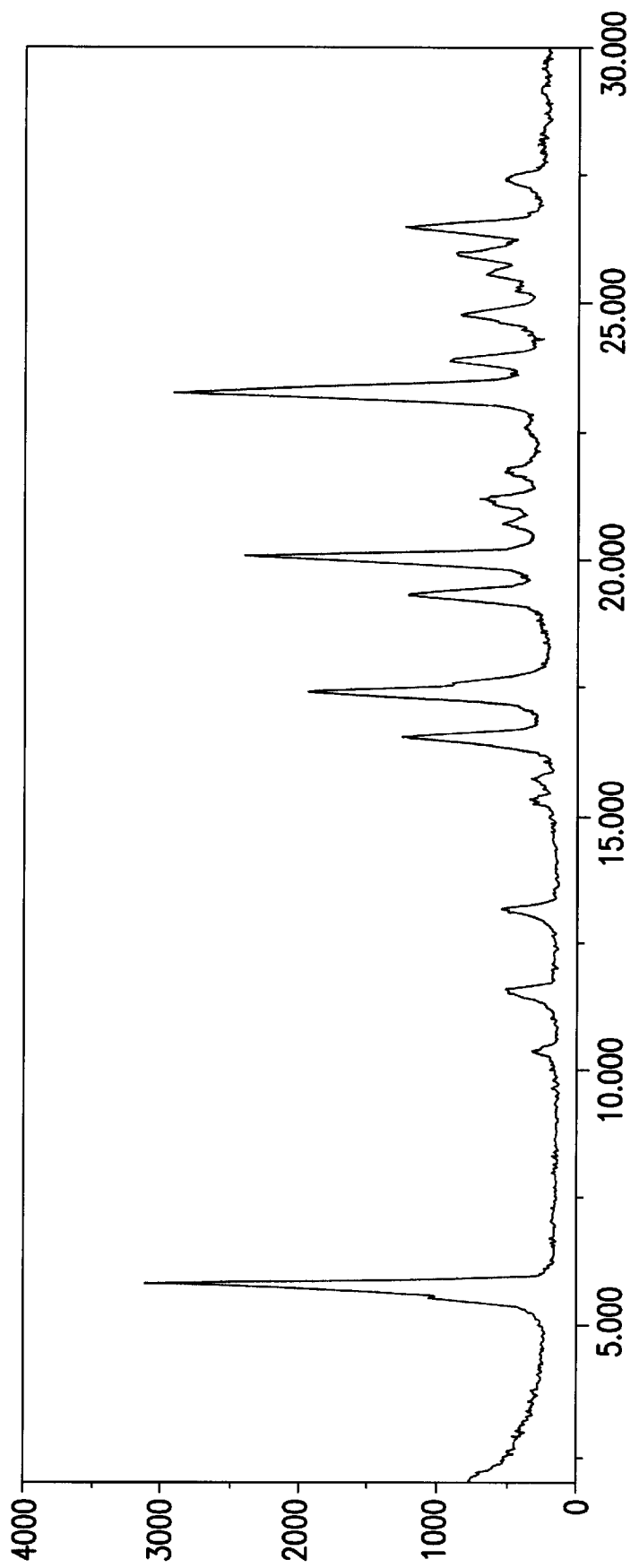
FIG. 2 is the powder X-ray diffraction pattern of Compound A type-II crystal obtained in Preparation 2.

The X-ray diffraction pattern of Compound A Type-II crystals thus obtained was measured with an X-ray powder diffractometer (RINT ULTIMA Type; manufactured by RIGAKU CORPORATION) at a tube voltage of 40 kV, and a tube electric current of 30 mA using CuKt wire in terms of diffraction angle (2θ). The diffraction pattern thereof is shown in FIG. 2. The diffraction angles in the X-ray powder diffraction pattern of Compound A Type-II crystals are about 5.9°, about 17.5°, about 19.4°, about 20.8°, about 23.3°, about 24.0°, and about 24.9°, and there are characteristic peaks at about 5.9°, about 17.5°, about 20.8°, and about 23.3°. The values of the diffraction angle (2θ) have the standard accuracy.

Preparation 3
Preparation of Drug Substance:
(1) The Compound A Type-I crystals obtained in Preparation 1 were micronized using a hammer mill (Sample Mill AP-S, manufactured by Hosokawa Micron Corporation, Japan) using a screen with opening diameter of 0.7 mm.
(2) Separately, the Compound A Type-I crystals obtained in Preparation 1 were micronized using a fluid energy mill (Single Truck Jet Mill FS-4, manufactured by SEISHIN ENTERPRISE CO., LTD., Japan) with compression air pressure of 7 kgf/cm².
(3) The particle sizes at the cumulative weight distribution value of 50% and 95% of each micronized granules thus obtained were measured using a laser diffraction particle size distribution analyzer (HELOS & RODOS (trademark), manufactured by SYMPATEC GmbH, Germany), and calculated from cumulative particle size distribution on volume basis by dry air dispersion method (dispersion air pressure: 1 atm). The particle size of the crystals obtained in (1) at the cumulative weight distribution value of 50% is not larger than 21 μm, and that at the cumulative weight distribution value of 95% was not larger than 75 μm. The particle size of the crystals obtained in (2) at the cumulative weight distribution value of 50% is not larger than 1.7 μm, and that at the cumulative weight distribution value of 95% was not larger than 3.8 μm. By either method for micronization, there can be obtained the crystals of Compound A having a particle size at the cumulative weight distribution value of 50% of not larger than 100 μm, and a particle size at the cumulative weight distribution value of 95% of not larger than 200 μm.

Experiment 1

Particle Size of the Drug Substance:

According to the prescription in Table 2, to a mixed powder of a drug substance or unmicronized crystals of Compound A, lactose, low substituted hydroxypropylcellulose and hydroxypropylcellulose was added water with stirring to give the granules (kneading granulation), which are dried, and regulated in size to give the granules. The granules thus obtained were mixed with crystalline cellulose, light anhydrous silicic acid and magnesium stearate, and compressed to give the tablets containing 1 mg of the drug substance or the unmicronized crystals of Compound A each. As a drug substance, ones micronized using a hammer mill (Sample Mill AP-S manufactured by Hosokawa Micron Corporation, Japan) using a screen with opening diameter of 0.7 mm or 1.0 mm, or ones micronized using a fluid energy mill (Single Truck Jet Mill FS-4, manufactured by SEISHIN ENTERPRISE CO., LTD., Japan) with compression air pressure of 7 kgf/cm², having various particle sizes as listed in Table 3 were used. The dissolution test of the tablets thus obtained was carried out according to the Thirteenth Edition of the Pharmacopoeia of Japan (Paddle method, 50 rpm, water 37° C., 900 ml), and the relation between the particle size of the drug substance and the dissolution thereof was evaluated by measuring the dissolution rate at 15 minutes. The results are shown in Table 3.

TABLE 2

| Components | | Weight (mg) |
|---|---|---|
| Granules | Drug substance or Unmicronized crystal of Compound A | 1 |
| | Lactose | 70 |
| | Low substituted hydroxypropylcellulose | 10 |
| | Hydroxypropylcellulose | 2.5 |
| External excipients | Crystalline cellulose | 15 |
| | Magnesium stearate | 1 |
| | Light anhydrous silicic acid | 0.5 |
| Total | | 100 |

TABLE 3

| | Method for micronization | Particle size (μm) of 50% cumulative weight distribution value | Particle size (μm) of 95% cumulative weight distribution value | Dissolution rate after 15 min. (%) |
|---|---|---|---|---|
| Exp. 1-1 | Fluid energy mill | 1.7 | 3.8 | 100 |
| Exp. 1-2 | Hammer mill (screen opening diamter: 0.7 mm) | 9.4 | 43 | 97 |
| Exp. 1-3 | Hammer mill (screen opening diamter: 0.7 mm) | 17 | 42 | 100 |
| Exp. 1-4 | Hammer mill (screen opening diamter: 0.7 mm) | 21 | 75 | 99 |
| Exp. 1-5 | Hammer mill (screen opening diamter: 0.7 mm) | 12.5 | 45 | 100 |
| Exp. 1-6 | Hammer mill (screen opening diamter: 1.0 mm) | 45 | 144 | 96 |
| Comp. Exp. 1-1 | Unmicronized | 85 | 366 | 60 |

The tablets prepared using the drug substance having a particle size at the cumulative weight distribution value of 50% of not larger than 100 μm and a particle size at the cumulative weight distribution value of 95% of not larger than 200 μm showed a distribution rate of almost 100% at 15 minutes, which is good dissolution ability.

Experiment 2

Composition Ratio in the Granules by Weight of the Drug Substance and the Excipients Other than the Drug Substance:

To a mixed powder of the drug substance (ones used in the above Experiment 1-3 for Experiment 2-1 and Comparative Experiment 2-1, and one used in the above Experiment 1-2 for Experiment 2-2), lactose, and low substituted hydroxypropylcellulose was sprayed an aqueous solution of hydroxypropylcelluose using a fluid bed granulator and drier, and granulated and dried to give the granules. As shown in Table 4, there were prepared three kinds of granules, wherein the content of the excipients other than the drug substance in the granules was different such as 82.5 parts by weight (Experiment 2-1), 417 parts by weight (Experiment 2-2), and 834 parts by weight (Comparative Experiment 2-1) to 1 part by weight of the drug substance. To each granule were added a fixed amount of crystalline cellulose, light anhydrous silicic acid and magnesium stearate, and the mixture was compressed to give tablets. These tablets were stored under conditions of 40° C.–75% RH (relative humidity) for 4 months, and the content of all of the decomposition products derived from the drug substance was measured, and the increase thereof was calculated from the initial amount. The results are shown in Table 5.

TABLE 4

| | Component | Exp. 2-1 | Exp. 2-2 | Comp. Exp. 2-1 |
|---|---|---|---|---|
| Granules | Drug substance | 1 | 0.2 | 0.1 |
| | Lactose | 70 | 70.8 | 70.9 |
| | Low substituted hydroxypropyl-cellulose | 10 | 10 | 10 |
| | Hydroxypropyl-cellulose | 2.5 | 2.5 | 2.5 |
| External excipients | Crystalline cellulose | 15 | 15 | 15 |
| | Magnesium stearate | 1 | 1 | 1 |
| | Light anhydrous silicic acid | 0.5 | 0.5 | 0.5 |
| Total (mg) | | 100 | 100 | 100 |
| Parts in the granules by weight of excipients other than drug substance of 1 part by weight of drug substance | | 82.5 | 417 | 834 |

TABLE 5

| | Exp. 2-1 | Exp. 2-2 | Comparative Exp. 2-1 |
|---|---|---|---|
| Increase (%) of amount of all of the decomposition products | 0.20 | 0.69 | 1.45 |

In the tablets of Experiment 2-1 and 2-2, the amount of all of the decomposition products are produced less, as compared with the tablets of Comparative Experiment 2-1, which contains more than 500 parts in the granules by weight of the excipients other than the drug substance to 1 part by weight of the drug substance, by which it is proven that the chemical stability of the drug substance per se in the tablets of Experiments 2-1 and 2-2 is high.

Experiment 3
Composition Ratio in the Granules by Weight of the Drug Substance and the Excipients Other than the Drug Substance:

According to the prescription of Table 6, to a mixed powder of lactose and low substituted hydroxypropylcellulose was added a solution of hydroxypropylcellulose in purified water to give granules (kneading granulation), which were dried and regulated in size to give the granules of the external excipients.

TABLE 6

| Components | | Weight (mg) |
|---|---|---|
| Granules of external excipients | Lactose | 71 |
| | Low substituted hydroxypropylcellulose | 10 |
| | Hydroxypropylcellulose | 2.5 |
| Total | | 83.5 |

To a mixed powder of the drug substance (one used in the above Experiment 1-4), lactose and low substituted hydroxypropylcellulose was added a solution of hydroxypropylcellulose in purified water to give granules (kneading granulation), which were dried and regulated in size to give the granules. Form this granules, there were obtained 4 kinds of the granules wherein the content of the excipients other than the drug substance in the granules was different such as 416.5 parts by weight (Experiment 4-1, Experiment 4-2), 1001 parts by weight (Comparative Experiment 4-1), 1251.5 parts by weight (Comparative Experiment 4-2), to 1 part by weight of the drug substance. To 4 kinds of the granules were added the granules of the external excipients obtained according to the prescription of the above Table 6, crystalline cellulose, light anhydrous silicic acid and magnesium stearate, and the mixture was compressed to give tablets containing 0.1 mg of the drug substance each as well as 1.87 part by weight of the external excipients to 1 part by weight of the granules (Experiment 3-1), tablets containing 0.2 mg of the drug substance each as well as 2.59 parts by weight of the external excipients to 1 part by weight of the granules (Experiment 3-2), tablets containing 0.1 mg of the drug substance each as well 0.20 part by weight of the external excipients to 1 part by weight of the granules (Comparative Experiment 3-1), and tablets containing 0.2 mg of the drug substance each as well 0.20 part by weight of the external excipients to 1 part by weight of the granules (Comparative Experiment 3-2). These tablets were stored under conditions of 40° C.–75% RH (relative humidity) for one month, and the content of all of the decomposition products derived from the drug substance was measured by high performance liquid chromatography, and the increase thereof was calculated from the initial amount. The results are shown in Table 8.

TABLE 7

| | Component | Exp. 3-1 | Exp. 3-2 | Comp. Exp. 3-1 | Comp. Exp. 3-2 |
|---|---|---|---|---|---|
| Granules | Drug substance | 0.1 | 0.2 | 0.1 | 0.2 |
| | Lactose | 35.4 | 70.8 | 85.1 | 212.8 |
| | Low substituted hydroxypropyl-cellulose | 5 | 10 | 12 | 30 |
| | Hydroxypropyl-cellulose | 1.25 | 2.5 | 3 | 7.5 |
| External excipients | Granules of external excipients | 58.45 | 167 | — | — |
| | Crystalline cellulose | 18 | 45 | 18 | 45 |
| | Magnesium stearate | 1.2 | 3 | 1.2 | 3 |
| | Light anhydrous silicic acid | 0.6 | 1.5 | 0.6 | 1.5 |
| Total (mg) | | 120 | 300 | 120 | 300 |
| Parts in the granules by weight of excipients other than drug substance to 1 part by weight of drug substance | | 416.5 | 416.5 | 1001 | 1251.5 |
| Parts by weight external excipients to 1 part by weight of granules | | 1.87 | 2.59 | 0.20 | 0.20 |

TABLE 8

| | Exp. 3-1 | Exp. 3.2 | Comp. Exp. 3-1 | Comp. Exp. 3-2 |
|---|---|---|---|---|
| Increase (%) of amount of all of the decomposition products | 0.75% | 0.83% | 1.31% | 1.76% |

In the tablets of Experiments 3-1 and 3-2, the amount of all of the decomposition products are produced less, as compared with the tablets of Comparative Experiments 3-1 and 3-2, by which it is proven that the chemical stability of the drug substance per se in the tablets of Experiments 3-1 and 3-2 is high.

Experiment 4
Premixing During the Preparation of Granules:

According to the prescription of Table 9, there were obtained tablets containing 0.05 mg of the drug substance (one used in the above Experiment 1-5) per each. When preparing the granules, the drug substance was previously mixed and micronized with lactose using a mixer sieve (a stainless sieve of 50 mesh=Experiment 3-1) or using a granulator (a hammer mill=Experiment 3-2), and thereto were added low substituted hydroxypropylcellulose and hydroxypropylcellulose. Water was added with stirring to the mixture to give granules (kneading granulation), and dried and regulated in size to give the granules. To the granules thus obtained were added and mixed crystalline cellulose, light anhydrous silicic acid and magnesium stearate, and the mixture was compressed to give the tablets. The content uniformity of the tablets thus obtained was tested according Content Uniformity Test in the Thirteenth Edition of the Pharmacopoeia of Japan (whereby the result of below 15% is considered adequate). The results are shown in Table 10.

TABLE 9

| Components | | Weight (mg) |
|---|---|---|
| Granules | Drug substance | 0.05 |
| | Lactose | 17.7 |
| | Low substituted hydroxypropylcellulose | 2.5 |
| | Hydroxypropylcellulose | 0.625 |
| External excipients | Crystalline cellulose | 3.75 |
| | Magnesium stearate | 0.25 |
| | Light anhydrous silicic acid | 0.125 |
| Total | | 25 |

TABLE 10

| | Exp. 4-1 | Exp. 4-2 |
|---|---|---|
| Method for premixing | Stainless sieve | Hammer mill |
| Content uniformity (%) | 10.0 | 4.0 |

In Content Uniformity Test in the Thirteenth Edition of the Pharmacopoeia of Japan, the result of below 15% is considered adequate. Since the results of the uniformity test of the tablets of Experiments 4-1 and 4-2 were both below 15%, the uniformity of the content of the drug substance was reserved in these tablets.

Example 1

According to the prescription of Table 1 1, there were obtained the tablets containing 1 mg of the drug substance (one used in Experiment 1-3 as mentioned above) each. When preparing the granules, the drug substance was previously mixed and sieved with lactose using a hammer mill, and thereto were added low substituted hydroxypropylcellulose and hydroxypropylcellulose. Water was added to the mixture with stirring to give the granules (kneaded granulation), which ware dried and regulated in size to give granules having a particle size of not larger than 250 μm at the cumulative weight distribution value of 50%, and a particle size of not larger than 600 μm at the cumulative weight distribution value of 95%. The granules thus obtained were mixed with crystalline cellulose, light anhydrous silicic acid and magnesium stearate, and the mixture was compressed to give the tablets. The tablets thus obtained had a suitable size and the content uniformity and the stability of the drug substance were reserved, and the dissolution of the drug substance from the tablets was rapid.

TABLE 11

| Components | | Weight (mg) |
|---|---|---|
| Granules | Drug substance | 1 |
| | Lactose | 70 |
| | Low substituted hydroxypropylcellulose | 10 |
| | Hydroxypropylcellulose | 2.5 |
| External excipients | Crystalline cellulose | 15 |
| | Magnesium stearate | 1 |
| | Light anhydrous silicic acid | 0.5 |
| Total | | 100 |

Example 2

According to the prescription of Table 12, there were obtained tablets containing 0.1 mg of the drug substance (one used in Experiment 1-5 as mentioned above) each. When preparing the granules, the drug substance was previously mixed and sieved with lactose using a hammer mill, and thereto were added low substituted hydroxypropylcellulose and hydroxypropylcellulose. Water was added to the mixture with stirring to give the granules (kneaded, granulation), and dried and regulated in size to give the granules having a particle size of not larger than 250 μm at the cumulative weight distribution value of 50%, and a particle size of not larger than 600 μm at the cumulative weight distribution value of 95%. The granules thus obtained were mixed with crystalline cellulose, light anhydrous silicic acid and magnesium stearate, and the mixture was compressed to give the tablets. The tablets thus obtained had a suitable size and the content uniformity and the stability of the drug substance were reserved, and the dissolution of the drug substance from the tablets was rapid.

TABLE 12

| Components | | Weight (mg) |
|---|---|---|
| Granules | Drug substance | 1 |
| | Lactose | 35.3 |
| | Low substituted hydroxypropylcellulose | 5 |
| | Hydroxypropylcellulose | 1.25 |
| External excipients | Crystalline cellulose | 7.5 |
| | Magnesium stearate | 0.5 |
| | Light anhydrous silicic acid | 0.25 |
| Total | | 50 |

Example 3

According to the prescription of Table 13, there were obtained tablets containing 0.05 mg of the drug substance (one used in Experiment 1-5 as mentioned above) each. When preparing the granules, the drug substance was previously mixed and sieved with lactose using a hammer mill, and thereto were added low substituted hydroxypropylcellulose and hydroxypropylcellulose. Water was added to the mixture with stirring to give the granules (kneaded granulation), and dried and regulated in size to give the granules having a particle size of not larger than 250 μm at the cumulative weight distribution value of 50%, and a particle size of not larger than 600 μm at the cumulative weight distribution value of 95%. The granules thus obtained were mixed with crystalline cellulose, light anhydrous silicic acid and magnesium stearate, and the mixture was compressed to give the tablets. The tablets thus obtained had a suitable size and the content uniformity and the stability of the drug substance were reserved, and the dissolution of the drug substance from the tablets was rapid.

TABLE 13

| Components | | Weight (mg) |
|---|---|---|
| Granules | Drug substance | 0.05 |
| | Lactose | 17.7 |
| | Low substituted hydroxypropylcellulose | 2.5 |
| | Hydroxypropylcellulose | 0.625 |
| External excipients | Crystalline cellulose | 3.75 |
| | Magnesium stearate | 0.25 |
| | Light anhydrous silicic acid | 0.125 |
| Total | | 25 |

Example 4

According to the prescription of Table 14, there were obtained tablets containing 0.2 mg of the drug substance (one used in Experiment 1-3 as mentioned above) each. To a mixed powder of the drug substance, low substituted hydroxypropylcellulose and hydroxypropylcellulose was added water with stirring to give the granules (kneaded granulation), which were dried and regulated in size to give the granules having a particle size of not larger than 350 μm at the cumulative weight distribution value of 50%, and a particle size of not larger than 1000 μm at the. cumulative weight distribution value of 95%. The granules thus obtained were mixed with crystalline cellulose, light anhydrous silicic acid and magnesium stearate, and the mixture was compressed to give the tablets. The tablets thus obtained had a suitable size and the content uniformity and the stability of the drug substance were reserved, and the dissolution of the drug substance from the tablets was rapid.

TABLE 14

| Components | | Weight (mg) |
|---|---|---|
| Granules | Drug substance | 0.2 |
| | Lactose | 70.8 |
| | Low substituted hydroxypropylcellulose | 10 |
| | Hydroxypropylcellulose | 2.5 |
| External excipients | Crystalline cellulose | 15 |
| | Magnesium stearate | 1 |
| | Light anhydrous silicic acid | 0.5 |
| Total | | 100 |

Example 5

According to the prescription of Table 15, to a mixed powder of the drug substance (one used in Experiment 1-4 as mentioned above), lactose, and low substituted hydroxypropylcellulose was sprayed a solution of hydroxypropylcellulose in purified water to give the granules (fluid bed granulation), which were dried and regulated in size to give the granules. The granules thus obtained were mixed with crystalline cellulose and light anhydrous silicic acid, and the mixture was compressed to give the tablets containing 0.5 mg of the drug substance each. The tablets thus obtained had a suitable size and the content uniformity and the stability of the drug substance were reserved, and the dissolution of the drug substance from the tablets was rapid.

TABLE 15

| Components | | Weight (mg) |
|---|---|---|
| Granules | Drug substance | 0.5 |
| | Lactose | 84.7 |
| | Low substituted hydroxypropylcellulose | 12 |
| | Hydroxypropylcellulose | 3 |
| External excipients | Crystalline cellulose | 18 |
| | Magnesium stearate | 1.2 |
| | Light anhydrous silicic acid | 0.6 |
| Total | | 120 |

Example 6

According to the prescription of Table 16, to a mixed powder of the drug substance (one used in Experiment 1-4 as mentioned above), lactose, low substituted hydroxypropylcellulose was sprayed a solution of hydroxypropylcellulose in purified water to give the granules (fluid bed granulation), which were dried and regulated in size to give the granules. The granules thus obtained were mixed with granules of the external excipients, crystalline cellulose, and light anhydrous silicic acid, and the mixture was compressed to give the tablets containing 0.5 mg of the drug substance each. The tablets thus obtained had a suitable size and the content uniformity and the stability of the drug substance were reserved, and the dissolution of the drug substance from the tablets was rapid.

TABLE 16

| Components | | Weight (mg) |
|---|---|---|
| Granules | Drug substance | 0.5 |
| | Lactose | 169.39 |
| | Low substituted hydroxypropylcellulose | 24 |
| | Hydroxypropylcellulose | 6 |
| External excipients | Crystalline cellulose | 36 |
| | Magnesium stearate | 2.4 |
| | Light anhydrous silicic acid | 1.2 |
| Total | | 240 |

Example 7

According to the prescription of Table 17, to a mixed powder of lactose and low substituted hydroxypropylcellulose was sprayed a solution of hydroxypropylcellulose in purified water to give the granules (fluid bed granulation), which were dried and regulated in size to give the granules of the external excipients.

TABLE 17

| Components | | Weight (mg) |
|---|---|---|
| Granules of External excipients | Lactose | 71 |
| | Low substituted hydroxypropylcellulose | 10 |
| | Hydroxypropylcellulose | 2.5 |
| Total | | 83.5 |

According to the prescription of Table 18, to a mixed powder of the drug substance (one used in Experiment 1-4 as mentioned above), lactose, and low substituted hydroxypropylcellulose was sprayed a solution of hydroxypropylcellulose in purified water to give the granules (fluid bed granulation), which were dried and regulated in size to give the granules. The granules thus obtained were mixed with the granules of the external excipients obtained according to the prescription of Table 17, crystalline cellulose, and light anhydrous silicic acid, and the mixture was compressed to give the tablets containing 0.1 mg of the drug substance each. The tablets thus obtained had a suitable size and the content uniformity and the stability of the drug substance were reserved, and the dissolution of the drug substance from the tablets was rapid.

TABLE 18

| Components | | Weight (mg) |
|---|---|---|
| Granules | Drug substance | 0.1 |
| | Lactose | 35.4 |
| | Low substituted hydroxypropylcellulose | 5 |
| | Hydroxypropylcellulose | 1.25 |
| External excipients | Granules of external excipients | 58.45 |
| | Crystalline cellulose | 18 |
| | Magnesium stearate | 1.2 |
| | Light anhydrous silicic acid | 0.6 |
| Total | | 120 |

Example 8

According to the prescription of Table 19, to a mixed powder of the drug substance (one used in Experiment 1-4 as mentioned above), lactose, and low substituted hydroxypropylcellulose was sprayed a solution of hydroxypropylcellulose in purified water to give the granules (fluid bed granulation), which were dried and regulated in size to give the granules. The granules thus obtained were mixed with the granules of the external excipients, crystalline cellulose, and light anhydrous silicic acid, and the mixture was compressed to give the tablets containing 0.2 mg of the drug substance each. The tablets thus obtained had a suitable size and the content uniformity and the stability of the drug substance were reserved, and the dissolution of the drug substance from the tablets was rapid.

TABLE 19

| Components | | Weight (mg) |
|---|---|---|
| Granules | Drug substance | 0.2 |
| | Lactose | 70.8 |
| | Low substituted hydroxypropylcellulose | 10 |
| | Hydroxypropylcellulose | 2.5 |
| External excipients | Granules of external excipients | 167 |
| | Crystalline cellulose | 45 |
| | Magnesium stearate | 3 |
| | Light anhydrous silicic acid | 1.5 |
| Total | | 300 |

INDUSTRIAL APPLICABILITY

The crystals of Compound A of the present invention having a particle size of not larger than 100 μm at the cumulative weight distribution value of 50% and a particle size of not larger than 200 μm at the cumulative weight distribution value of 95% (the drug substance of the present invention) are useful as a starting material for preparation. The drug substance of the present invention exhibits a potent $\beta_3$-adrenergic receptor-stimulating activity with excellent adrenoceptor selectivity, and hence, it is useful in the prophylaxis or treatment of obesity or diabetic mellitus. The preparation containing the drug substance of the present invention is an excellent preparation being characteristic in that the size (volume) of the preparation, the content uniformity of the drug substance, and the stability of the drug substance are secured, and that the dissolution of the drug substance therefrom is rapid.

What is claimed is:

1. A crystal of [3-[(2R)-[[(2R)-(3-chlorophenyl)-2-hydroxyethyl]-amino]propyl]-1H-indol-7-yloxy]acetic acid.

2. A crystal of [3-[(2R)-[[(2R)-(3-chlorophenyl)-2-hydroxyethyl]-amino]propyl]-1H-indol-7-yloxy]acetic acid, which shows characteristic diffraction peaks at the diffraction angles (2θ) of about 5.9°, about 17.9°, about 20.5°, and about 24.0° in the X-ray powder diffraction pattern.

3. The crystal according to claim 1, wherein the particle size thereof is not larger than 100 μm at the cumulative weight distribution value of 50%, and not larger than 200 μm at the cumulative weight distribution value of 95%.

4. A granular composition comprising
the crystal according to claim 3, and
a pharmaceutically acceptable excipient.

5. The granular composition according to claim 4, which consists of
(a) said crystal,
(b) a filler,
(c) a disintegrant, and
(d) a binder.

6. The granular composition according to claim 5, wherein the total weight of the filler, the disintegrant and the binder is less than 500 parts by weight to 1 part by weight of said crystal.

7. A solid composition which comprises the granular composition according to claim 4, and external excipients.

8. The solid composition according to claim 7, wherein the content of the crystal according to claim 3 is less than 2 mg per dosage unit.

9. The solid composition according to claim 7, which is in the form of a tablet.

10. A tablet which is prepared by compression tableting the granule as set forth in claim 4.

11. The tablet according to claim 10, wherein the content of the crystal as set forth in claim 3 is not more than 2 mg per dosage unit.

12. A tablet that is prepared by adding external excipients to the granule as set forth in claim 4, followed by compression tableting the mixture.

13. The tablet according to claim 12, wherein the content of the crystal as set forth in claim 3 is not more than 2 mg per dosage unit.

14. A pharmaceutical composition comprising:
an effective amount of the crystal according to claim 3; and
a pharmaceutically acceptable carrier.

15. A method of treating diabetes mellitus in a patient in need thereof, comprising administering an effective amount of the crystal of claim 3 to said patient.

16. A method of treating obesity in a patient in need thereof, comprising administering an effective amount of the crystal of claim 3 to said patient.

17. The crystal according to claim 3, wherein said particle size is not larger than 21 μm at the cumulative weight distribution value of 50%, and not larger than 75 μm at the cumulative weight distribution value of 95%.

* * * * *